(12) United States Patent
Jou et al.

(10) Patent No.: US 9,287,508 B1
(45) Date of Patent: Mar. 15, 2016

(54) LIGHT-EMITTING MATERIAL

(71) Applicant: National Tsing Hua University, Hsinchu (TW)

(72) Inventors: Jwo-Huei Jou, Hsinchu (TW); Sudhir Kumar, Hsinchu (TW); Justin Thomas Koil Pitchai Rajapandian, Hsinchu (TW)

(73) Assignee: National Tsing Hua University (TW)

( * ) Notice: Subject to any disclaimer, the term of this patent is extended or adjusted under 35 U.S.C. 154(b) by 0 days.

(21) Appl. No.: 14/512,449

(22) Filed: Oct. 12, 2014

(30) Foreign Application Priority Data

Aug. 22, 2014 (TW) .............................. 103129018 A

(51) Int. Cl.
| | |
|---|---|
| *C07C 255/52* | (2006.01) |
| *H01L 51/00* | (2006.01) |
| *H01L 51/50* | (2006.01) |
| *C07C 211/54* | (2006.01) |
| *C09K 11/06* | (2006.01) |

(52) U.S. Cl.
CPC .......... *H01L 51/0058* (2013.01); *C07C 211/54* (2013.01); *C07C 255/52* (2013.01); *C09K 11/06* (2013.01); *H01L 51/0059* (2013.01); *H01L 51/5004* (2013.01); *H01L 51/5028* (2013.01); *C09K 2211/1007* (2013.01); *C09K 2211/1011* (2013.01); *C09K 2211/1014* (2013.01)

(58) Field of Classification Search
CPC .......................... H01L 51/0058; C07C 255/52
See application file for complete search history.

(56) References Cited

PUBLICATIONS

Wu et al. "Synthesis, Structure, and Photophysical Properties of Dibenzo[de,mn]naphthacenes" Angewandte Chemie International Edition, 2010, vol. 49, pp. 7059-7062.*

* cited by examiner

*Primary Examiner* — Joseph Kosack

(57) ABSTRACT

The present invention provides a novel light-emitting material, which is a blue fluorescent material performs a high quantum yield of ~86%, and can be doped into a host light-emitting layer of an organic light emitting diode (OLED) for being a guest light-emitting material, so as to increase the external quantum efficiency, the power efficiency and the current efficiency of the OLED. Most importantly, a variety of experiment results have proved that the OLED having the novel light-emitting material can emit a deep blue light with CIE coordinates of (0.156, 0.055). Moreover, the experiment results also proved that the novel light-emitting material can be applied in fabricating OLED through dry process and/or wet process; so that, the novel light-emitting material is helpful to the low-cost mass production of OLEDs.

2 Claims, 18 Drawing Sheets

Table 1

| Material | $T_m$ (°C) | $T_d$ (°C) | $\lambda_{PL}$ (nm) | $\lambda_{abs}$ (nm) ($\varepsilon_{max} \times 10^3$ M$^{-1}$ cm$^{-1}$) | PLQY ($\Phi_F$, %) | HOMO (eV) | LUMO (eV) |
|---|---|---|---|---|---|---|---|
| C3FLA-2 | 260 | 457 | 413, 434 | 383, 295 | 86 | 5.92 | 2.88 |
| C2FLA-1 | 232 | 394 | 401 | 373, 353 | 84 | 5.84 | 2.62 |
| CFLA-Ph2 | 188 | 391 | 428 | 395, 379, 328, 304 | 68 | 5.33 | 2.49 |

FIG. 3

Table 2

| Material | Doping Conc. (wt %) | Operating Voltage (V) | Power Efficiency (lm/W) | Current Efficiency (cd/A) | External Quantum Efficiency (%) | CIE Coordinates | Maximum luminance (cd/m²) |
|---|---|---|---|---|---|---|---|
| | | | @ 100 /1,000 cd/m² (Data marked "*" were obtained at 50 cd/m²) | | | | |
| C3FLA-2 | 100 | 9.2/- | 0.2/- | 0.5/- | 0.5/- | (0.158, 0.136)/- | 645 |
| | 1 | 4.5/6.0 | 1.6/0.7 | 2.2/1.3 | 5.8/3.3 | (0.156, 0.055)/(0.159, 0.064) | 1,253 |
| | 3 | 4.6/6.5 | 1.5/0.8 | 2.2/1.7 | 4.5/3.3 | (0.157, 0.062)/(0.160, 0.066) | 1,799 |
| | 5 | 5.0/7.1 | 1.4/0.6 | 2.2/1.5 | 3.2/2.2 | (0.157, 0.080)/(0.158, 0.080) | 1,843 |
| | 7 | 5.1/7.2 | 1.2/0.6 | 2.0/1.4 | 2.9/2.1 | (0.157, 0.080)/(0.158, 0.080) | 2,135 |
| C2FLA-1 | 100 | 7.6/- | 0.1/- | 0.2/- | 0.1/- | (0.199, 0.197)/- | 257 |
| | 1 | 4.9/6.7 | 0.4/0.2 | 0.6/0.4 | 3.1/1.5 | (0.159, 0.044)/(0.169, 0.081) | 929 |
| | 3 | 5.3/6.8 | 0.3/0.2 | 0.6/0.4 | 3.3/1.5 | (0.159, 0.042)/(0.168, 0.076) | 1,036 |
| | 5 | 4.9/6.7 | 0.5/0.2 | 0.8/0.5 | 3.0/1.3 | (0.159, 0.049)/(0.169, 0.088) | 1,381 |
| | 7 | 4.6/6.7 | 0.6/0.2 | 0.8/0.5 | 2.9/1.2 | (0.159, 0.051)/(0.170, 0.091) | 1,321 |
| CFLA-NPh₂ | 100 | 8.1/- | 0.1/- | 0.2/- | *0.2/- | *(0.170, 0.220)/- | 134 |
| | 1 | 3.8/5.1 | 3.2/1.9 | 3.8/3.0 | 4.0/3.6 | (0.145, 0.094)/(0.144, 0.089) | 2914 |
| | 3 | 3.8/5.2 | 3.4/1.9 | 4.1/3.1 | 4.3/3.7 | (0.152, 0.102)/(0.153, 0.097) | 3588 |
| | 5 | 3.9/5.3 | 3.3/1.8 | 4.0/2.9 | 3.8/3.0 | (0.152, 0.116)/(0.152, 0.109) | 4149 |
| | 7 | 4.0/5.5 | 3.0/1.5 | 3.8/2.7 | 3.6/2.7 | (0.152, 0.122)/(0.153, 0.115) | 3876 |

FIG. 9

Table 3

| Dopant (wt%) | ECL | Operating Voltage (V) | PE (lm/W) | CE (cd/A) | EQE (%) | CIE Coordinates | Maximum luminance (cd/m²) |
|---|---|---|---|---|---|---|---|
| | | | | @ 100 /1,000 cd/m² | | | |
| 1 | - | 5.8/7.0 | 1.2/0.6 | 2.2/1.3 | 6.5/3.7 | (0.156, 0.048)/(0.157, 0.049) | 2,111 |
| 1 | TAPC | 7.0/8.5 | 0.8/0.5 | 1.8/1.3 | 5.1/3.7 | (0.158, 0.048)/(0.159, 0.050) | 6,828 |
| 3 | - | 7.4/8.5 | 0.9/0.5 | 2.1/1.3 | 5.9/3.6 | (0.156, 0.048)/(0.157, 0.049) | 2,251 |
| 3 | TAPC | 8.3/9.7 | 0.7/0.5 | 1.9/1.4 | 4.7/3.5 | (0.157, 0.049)/(0.160, 0.053) | 6,824 |

FIG. 16

LIGHT-EMITTING MATERIAL

BACKGROUND OF THE INVENTION

1. Field of the Invention

The present invention relates to the technology field of OLEDs, and more particularly to a light-emitting material capable of facilitating an OLED emit deep blue light.

2. Description of the Prior Art

It is well known that organic light emitting diode (OLED) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device has become a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added into the OLEDs for increasing the current efficiency and power efficiency of the OLEDs. For example, the organic light emitting diode (OLED) 1' shown as FIG. 1 is consisted of: a cathode 11', an electron injection layer 13', a light emitting layer 14', a hole transport layer 16', and an anode 18'.

In fundamental principle, OLED 1' would emit light after a differential voltage is applied between the anode 18' and the cathode 11', wherein the light is emitted as the excitons produced by the combination of electrons and holes diffuse into the light emitting layer 14'. According to theoretical speculation, the ration of the excitons with singlet excited state and the excitons with triplet excited state is 3:1. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit.

Fluorescent materials are broadly studied in the initial development of OLEDs, and the OLED having first generation blue fluorescent material performs a maximum EQE (External Quantum Efficiency) of 5%. Although the first generation blue material shows the advantages of high thermal stability and reliable material life, the OLED having the first generation blue material can merely emit a baby blue light, but cannot emit a pure blue light and/or a deep blue light. Typical blue fluorescent material is made of distyrylarylene (DSA) derivative and proposed by Idemitsu Kosan Company in Japan.

Flrpic (Bis[2-(4,6-difluorophenyl)pyridinato-C2,N](picolinato)iridium(III)) is an exemplary material of second generation blue phosphor material with the CIE coordinates of (0.17, 0.34). Moreover, by substituting the Pyrazoly Borate group for the secondary group of Picolinate in Flrpic, a novel blue phosphor material is manufactured by Professor Thompson, wherein the novel blue phosphor material is named FIr6 (iridium(III)bis(4',6'-difluorophenylpyridinato)tetrakis(1-pyraolyl)borate). The OLED having FIr6 as the light-emitting layer 14' is able to emit a blue light with CIE coordinates of (0.16, 0.26) and performs the power efficiency of 13.91 lm/w.

In spite of that, The OLED 1' having FIr6 still cannot emit a pure blue light and/or a deep blue light. Herein, the standard CIE coordinates of deep blue made by NTSC (National Television System Committee) is (0.14, 0.08).

In recent years, research papers proposed a variety of host light-emitting material made of carbazole derivatives, for example, CDBP (4,4'-bis(9-carbazolyl)-2,2-dimethyl-biphenyl). Experiment results have been proved that, OLED's EQE can reach 10.4% when CDBP and Flrpic are respectively used as the host light-emitting material and the guest light-emitting material. However, the aforesaid materials cannot be applied in the fabrication of commercial OLED due to their unreliable material life.

Accordingly, in view of the conventional blue light-emitting materials cannot used for manufacturing OLEDs having the advantages of high EQE, long life time and including the standard CIE coordinates of deep blue, the inventor of the present application has made great efforts to make inventive research thereon and eventually provided a novel light-emitting material for organic light emitting devices (OLEDs).

SUMMARY OF THE INVENTION

The primary objective of the present invention is to provide a novel light-emitting material, which is a blue fluorescent material performs a high quantum yield of ~86%, and can be doped into a host light-emitting layer of an organic light emitting diode (OLED) for being a guest light-emitting material, so as to increase the external quantum efficiency, the power efficiency and the current efficiency of the OLED. Most importantly, a variety of experiment results have proved that the OLED having the novel light-emitting material can emit a deep blue light with CIE coordinates of (0.156, 0.055). Moreover, the experiment results also proved that the novel light-emitting material can be applied in fabricating OLED through dry process and/or wet process; so that, the novel light-emitting material is helpful to the low-cost mass production of OLEDs.

Accordingly, in order to achieve the primary objective of the present invention, the inventor of the present invention provides a novel light-emitting material, wherein the blue fluorescent material is a molecular compound formed by completing a sonogashira coupling reaction of at least one polycyclic aromatic hydrocarbons (PAHs) and at least one benzene derivative.

According to one embodiment of the novel light-emitting material, wherein the polycyclic aromatic hydrocarbons is represented by following chemical formula 1:

[chemical formula 1]

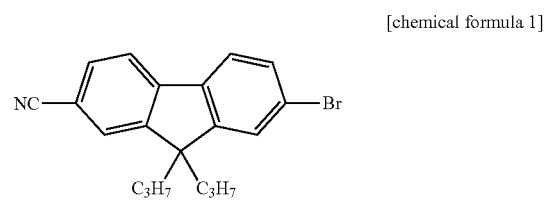

According to one embodiment of the novel light-emitting material, wherein the benzene derivative is represented by following chemical formula 2, chemical formula 3 and chemical formula 4:

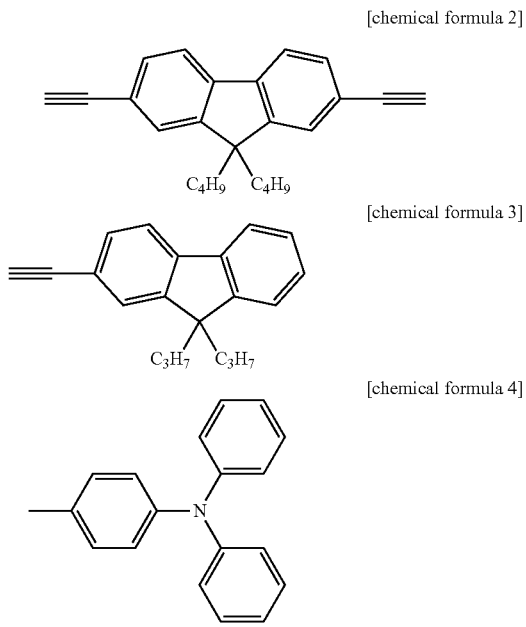

[chemical formula 2]

[chemical formula 3]

[chemical formula 4]

According to one embodiment of the novel light-emitting material, wherein the novel light-emitting material is represented by following chemical formula 5, chemical formula 6 and chemical formula 7:

FIG. 1 is a structure diagram of a conventional organic light emitting diode (OLED);

FIG. 2 is a schematic diagram of a sonogashira coupling reaction;

FIG. 3 shows a diagram of Table 1;

FIG. 4A shows overlapped photoluminescence spectra of C3FLA-2, Spiro-2CBP and CBP;

FIG. 4B shows overlapped photoluminescence spectra of C3FLA-2, TCTA and CBP;

FIG. 4C shows overlapped photoluminescence spectra C3FLA-2, SimCP2 and CBP;

FIG. 5 is a structure diagram of an organic light emitting diode (OLED) having the blue fluorescent material;

FIG. 6 shows a first energy band diagram of the OLED shown by FIG. 5;

FIG. 7 shows a second energy band diagram of the OLED shown by FIG. 5;

FIG. 8 shows a third energy band diagram of the OLED shown by FIG. 5;

FIG. 9 shows a diagram of Table 2;

FIG. 10 is a light spectra graph;

FIG. 11 shows a data plot of EQE versus current density;

FIG. 12 is a second structure diagram of the OLED;

FIG. 13 shows an energy band diagram of the OLED shown by FIG. 10;

FIG. 14 shows a data plot of luminance versus voltage;

FIG. 15 shows a data plot of EQE versus current density; and

FIG. 16 shows a diagram of Table 3.

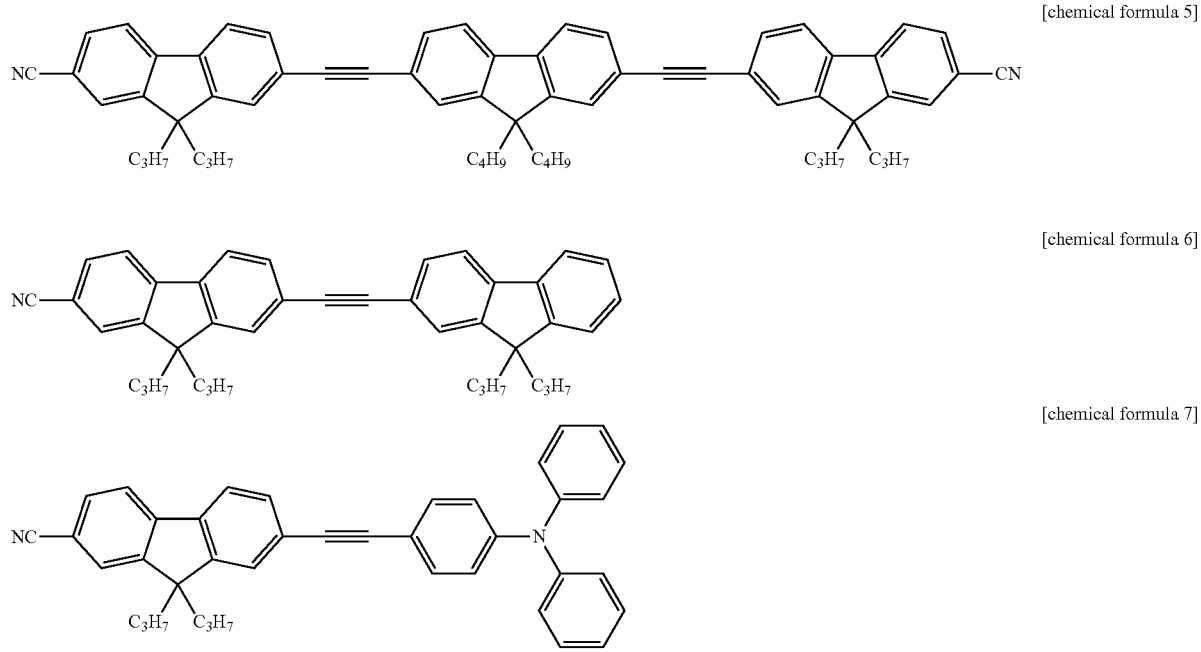

[chemical formula 5]

[chemical formula 6]

[chemical formula 7]

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

DETAILED DESCRIPTION OF THE PREFERRED EMBODIMENTS

To more clearly describe a novel light-emitting material according to the present invention, embodiments of the present invention will be described in detail with reference to the attached drawings hereinafter.

Figure 1:
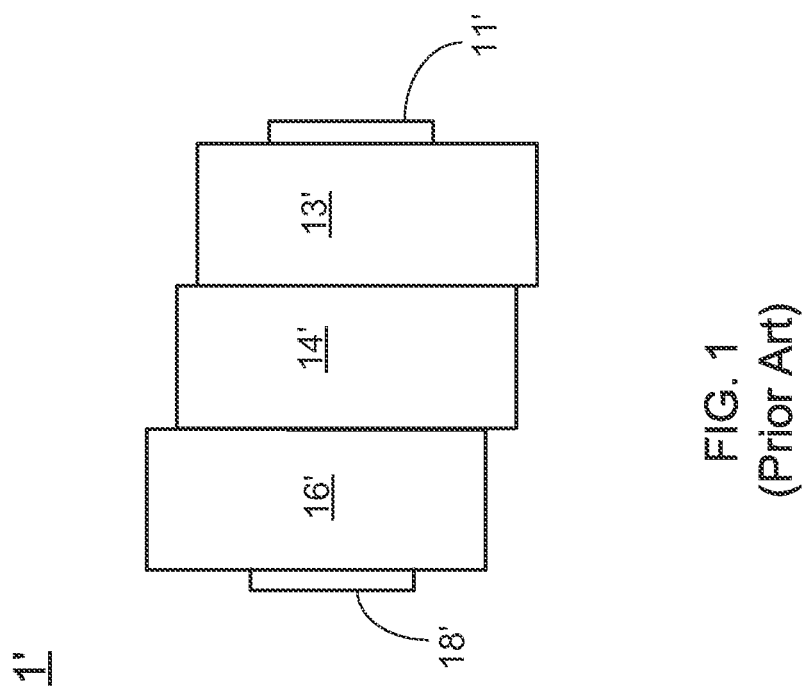
Figure 2:
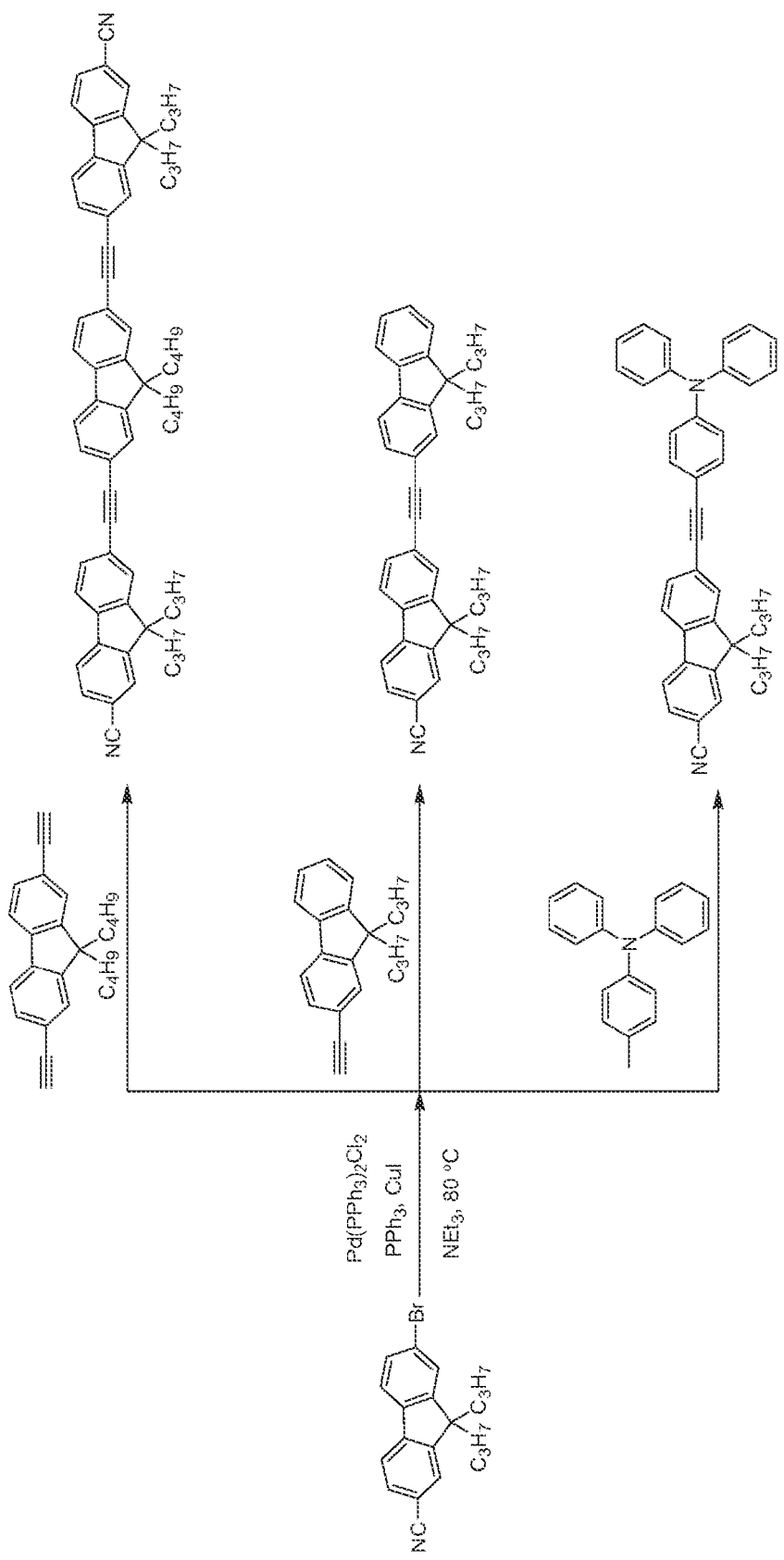

Please refer to FIG. 2, which illustrate the schematic diagram of a sonogashira coupling reaction. As shown in FIG. 2, the novel light-emitting material provided by the present invention is a molecular compound formed by completing a sonogashira coupling reaction of at least one polycyclic aromatic hydrocarbons (PAHs) and at least one benzene derivative, and the obtained molecular compound is then used as a blue fluorescent material. In the sonogashira coupling reaction, there are a plurality of catalytic agents be adopted, including Pd(PPh$_3$)$_2$Cl$_2$) (Palladium(II)bis(triphenylphosphine)dichloride), PPh$_3$ (Triphenylphosphine), CuI (Cuprous iodide), and Et$_3$N (Triethylamine).

Continuously referring to FIG. 2, the aforesaid polycyclic aromatic hydrocarbons is represented by following chemical formula 1:

[chemical formula 1]

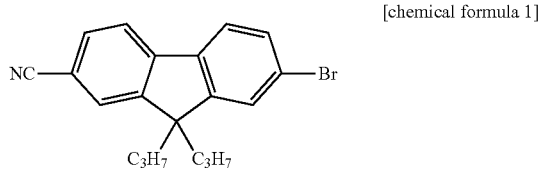

From the above-presented chemical formula, it is able to know that the chemical formula 1 represents the chemical structure of 7-Bromo-9,9-dipropyl-9H-fluorene-2-carbonitrile. Opposite to the PAHs, the chemical structure of the benzene derivative is represented by following chemical formula 2, chemical formula 3 and chemical formula 4:

[chemical formula 2]

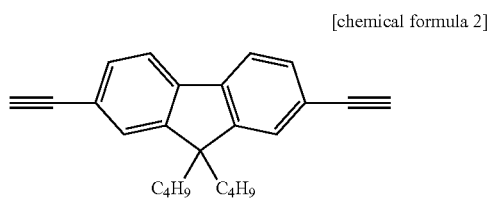

[chemical formula 3]

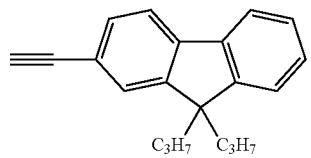

[chemical formula 4]

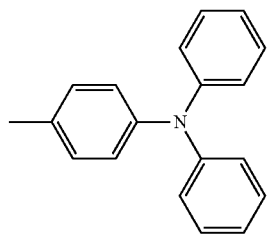

From the above-presented chemical formulas, it is able to know that the chemical formula 2 represents the chemical structure of 9,9-dibutyl-2,7-diethynyl-9H-fluorene, chemical formula 3 represents the chemical structure of 2-ethynyl-9,9-dibutyl-9H-fluorene, and chemical formula 4 represents the chemical structure of N-(4-methylphenyl)diphenylamine.

Referring to FIG. 2 again, after finishing the sonogashira coupling reaction under 80° C., the PAHs and the benzene derivative are synthesized to a blue fluorescent material capable of being doped into a host light-emitting layer of an organic light emitting diode (OLED) for being a guest light-emitting material, wherein the chemical structure of the obtained blue fluorescent material is represented by following chemical formula 5, chemical formula 6 and chemical formula 7:

[chemical formula 5]

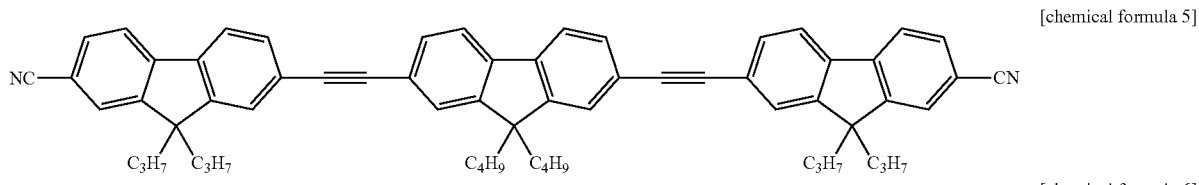

[chemical formula 6]

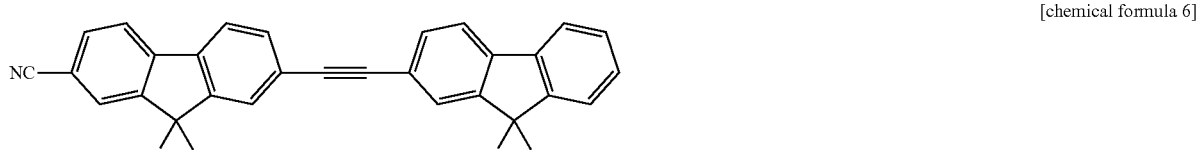

[chemical formula 7]

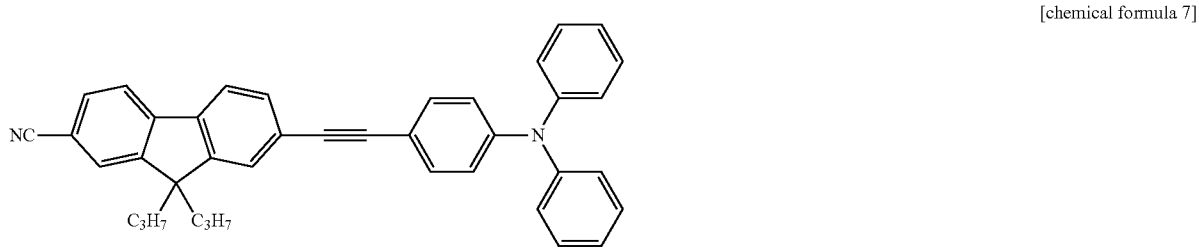

From the above-presented chemical formulas, it is able to know that the chemical formula 5 represents the chemical structure of 7,7'-((9,9-dibutyl-9H-fluorene-2,7-diyl)bis(ethyne-2,1-diyl))bis(9,9-dipropyl-9H-fluorene-2-carbonitrile) (coded as C3FLA-2 hereinafter), chemical formula 6 represents the chemical structure of 7-(2-(9,9-dipropyl-9H-fluoren-2-yl)ethynyl)-9,9-dipropyl-9H-fluorene-2-carbonitril (coded as C2FLA-1 hereinafter), and chemical formula 7 represents the chemical structure of 7-(2-(4-(Diphenylamino)phenyl)ethynyl)-9,9-dipropyl-9H-fluorene-2-carbonitril (coded as CFLA-NPh2 hereinafter).

With reference to FIG. 3, which illustrate the diagram of a table 1. In table 1, each of the three blue fluorescent materials (C3FLA-2, C2FLA-1 and CFLA-NPh2) have a high occupied molecular orbital energy level ($E_{HOMO}$ (ev)) and a lowest unoccupied molecular orbital energy level ($E_{LUMO}$ (ev)) of (5.92, 2.88), (5.84, 2.62), and (5.33, 2.49), respectively. In addition, the peak value of the photoluminescence spectra ($\lambda_{PL}$) of C3FLA-2, C2FLA-1 and CFLA-NPh2 are 413 (or 434) nm, 401 nm and 428 nm. Besides, the peak value of the absorption spectra ($\lambda_{abs}$) of C3FLA-2, C2FLA-1 and CFLA-NPh2 are 383 (or 295) nm, 373 (or 353) nm, and 395 (or 379, 328, 304) nm.

Table (1) records that the quantum yield of the C3FLA-2, C2FLA-1 and CFLA-NPh2 is 86%, 84% and 68%, wherein the C3FLA-2's quantum yield is greater than the conventional blue fluorescent material's and conventional blue phosphorescent material's quantum yield (~25% and ~75%). Herein, it needs to further explain that "$T_m$" and "$T_d$" written in table (1) represent melting temperature and decomposition temperature of the material.

Figure 4A:
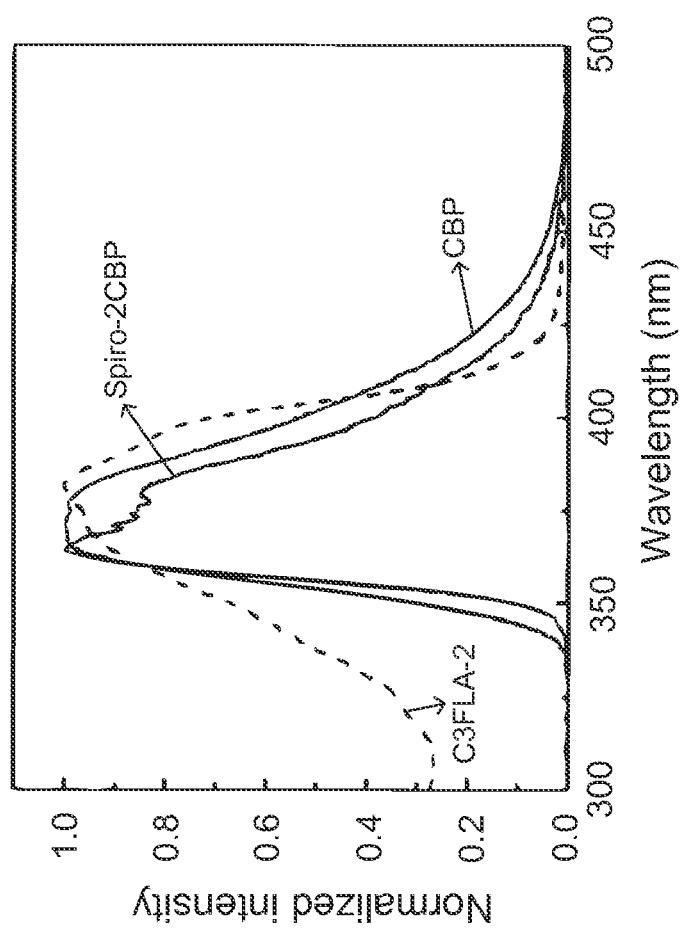
Figure 4B:
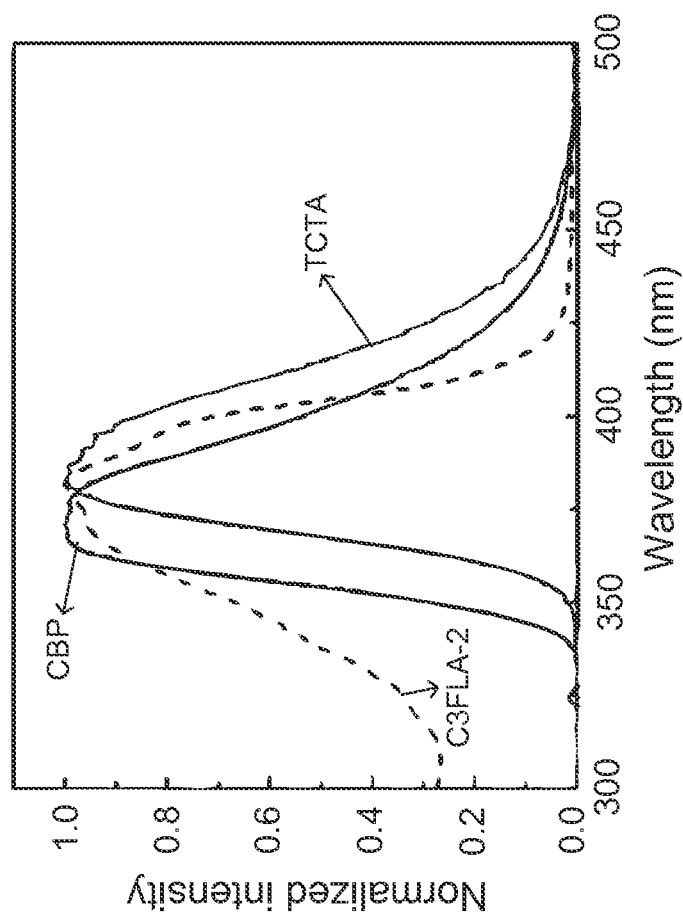
Figure 4C:
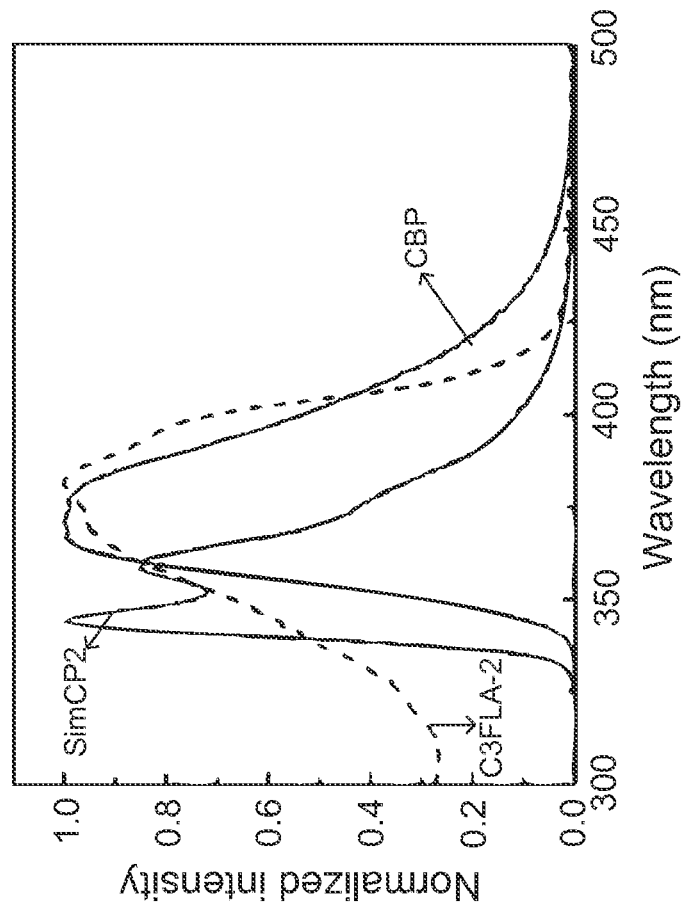

Subsequently, the photoluminescence spectrum of this novel light-emitting material is overlapped with a variety of photoluminescence spectra measured from different host light-emitting materials; wherein overlapped photoluminescence spectra of C3FLA-2, Spiro-2CBP and CBP are shown in FIG. 4A, overlapped photoluminescence spectra of C3FLA-2, TCTA and CBP are shown in FIG. 4B, and overlapped photoluminescence spectra C3FLA-2, SimCP2 and CBP are shown in FIG. 4C. As FIG. 4A shows, the C3FLA-2's photoluminescence spectrum is overlapped with the photoluminescence spectra of Spiro-2CBP and CBP. In addition, as shown in FIG. 4B, the C3FLA-2's photoluminescence spectrum is overlapped with the photoluminescence spectra of TCTA and CBP. Besides, as shown in FIG. 4C, the C3FLA-2's photoluminescence spectrum is overlapped with the photoluminescence spectra of SimCP2 and CBP. Therefore, from FIG. 4A, FIG. 4B and FIG. 4C, it can easily find that there has a largest overlapping range between the C3FLA-2's spectrum and the CBP's spectrum; that means CBP is the most suitable host light-emitting material for the novel light-emitting material (i.e., the blue fluorescent material) proposed by the present invention.

Figure 5:
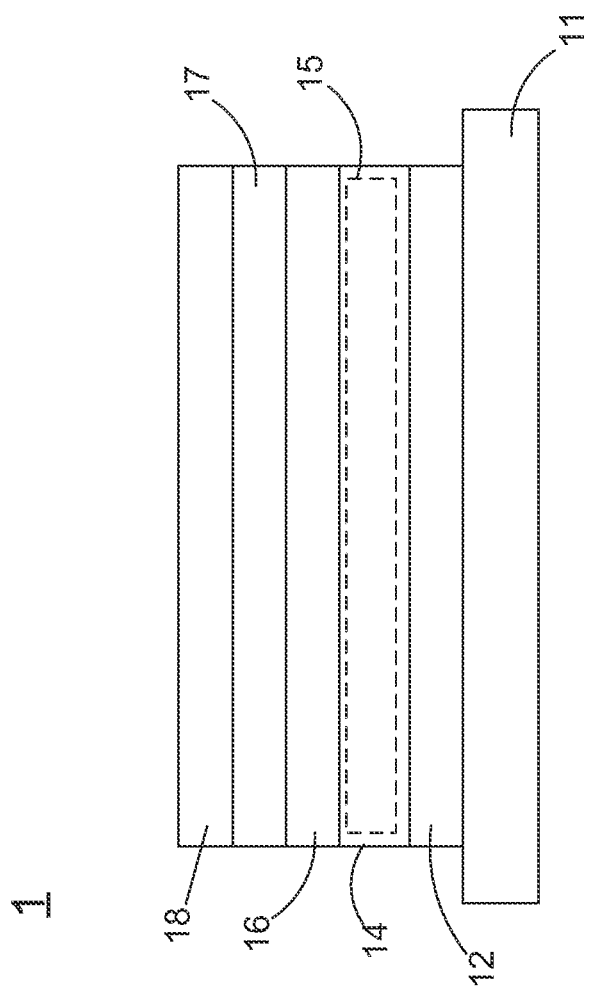

Continuously, for completing the comparisons of the three blue fluorescent materials (C3FLA-2, C2FLA-1 and CFLA-NPh2) in power efficiency (PE), current efficiency (CE) and external quantum efficiency (EQE), a variety of experiments have been finished. Please refer to FIG. 5, which illustrate a structure diagram of an organic light emitting diode (OLED) having the blue fluorescent material. As shown in FIG. 5, the OLED 1 having the blue fluorescent material consists of: an anode 11, a hole injection layer 12, a host light-emitting layer 14, a guest dye 15, an electron transport layer 16, an electron injection layer 17, and a cathode 18.

In the OLED 1, indium tin oxide (ITO) substrate, lithium fluorine (LiF), and aluminum (Al) are respectively used as the anode 11, the electron injection layer 17 and the cathode 18.

In addition, the hole injection layer 12 is made of poly(3,4-ethylenedioxythiophene) (PEDOT), and the electron transport layer 16 is formed by using 1,3,5-tris(N-phenylbenzimidazol-2-yl)benzene (TPBi) as the manufacturing material. Moreover, 4,4'-Bis(9H-carbazol-9-yl)biphenyl (CBP) is used for being the host light-emitting layer 14.

Figure 6:
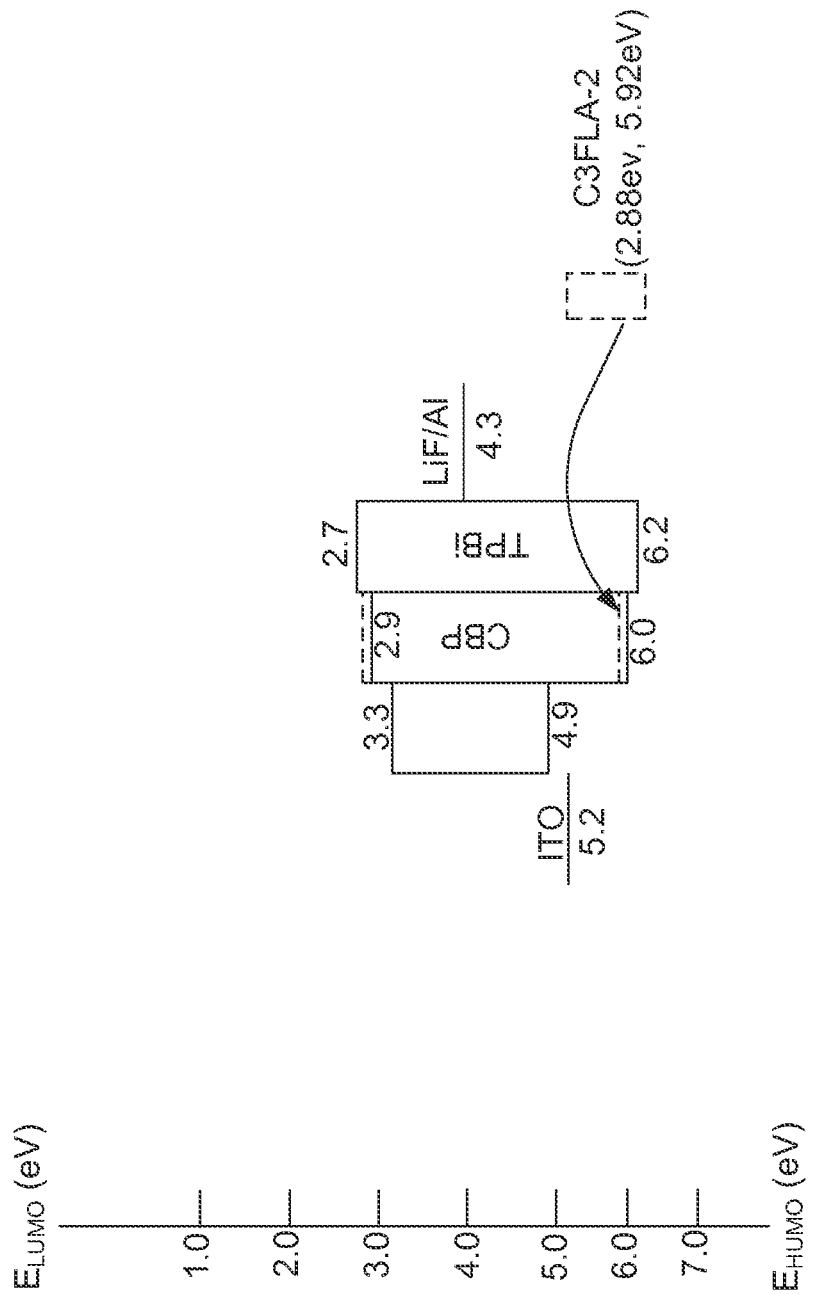
Figure 7:
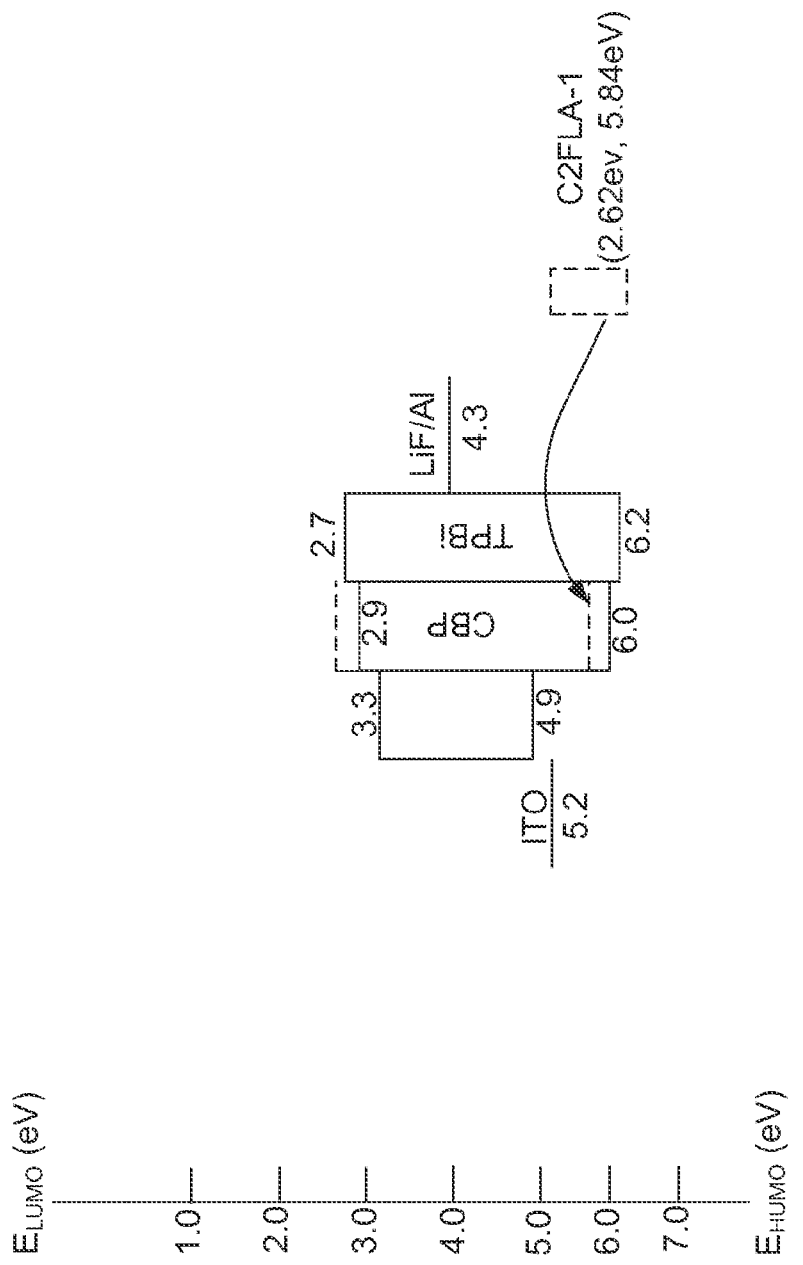
Figure 8:
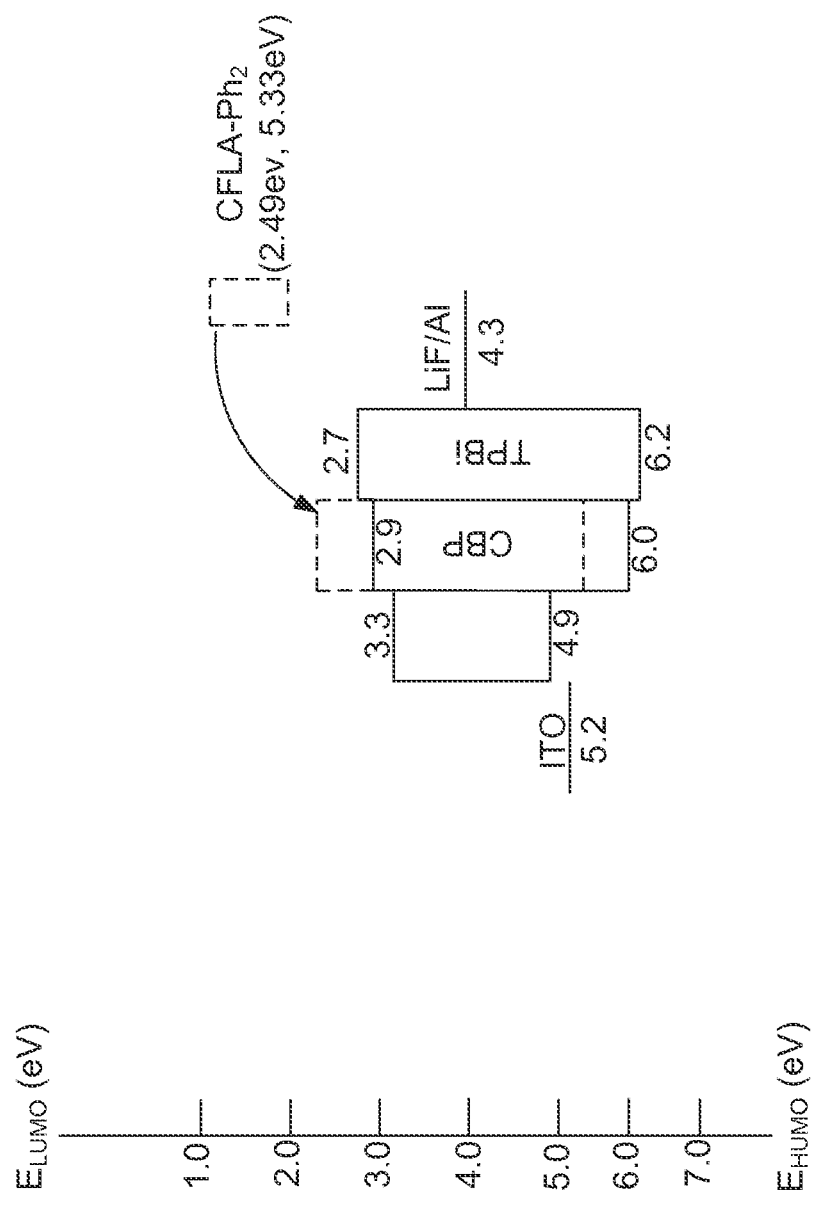

Referring to FIG. 5 again, and please simultaneously refer to FIG. 6, FIG. 7 and FIG. 8, wherein FIG. 6 shows a first energy band diagram of the OLED shown by FIG. 5, FIG. 7 shows a second energy band diagram of the OLED shown by FIG. 5, and FIG. 8 shows a third energy band diagram of the OLED shown by FIG. 5. As shown in FIG. 5 and FIG. 6, the host light-emitting material 14 (i.e., CBP) has the ($E_{LUMO}$, $E_{HOMO}$)=(2.9 eV, 6.0 eV), the guest dye 15 (i.e., the blue fluorescent material of C3FLA-2) has the ($E_{LUMO}$, $E_{HOMO}$)=(2.88 eV, 5.92 eV). Moreover, A shown in FIG. 5 and FIG. 7, the host light-emitting material 14 (i.e., CBP) has the ($E_{LUMO}$, $E_{HOMO}$)=(2.9 eV, 6.0 eV), the guest dye 15 (i.e., the blue fluorescent material of C2FLA-1) has the ($E_{LUMO}$, $E_{HOMO}$)=(2.62 eV, 5.84 eV). Furthermore, A shown in FIG. 5 and FIG. 8, the host light-emitting material 14 (i.e., CBP) has the ($E_{LUMO}$, $E_{HOMO}$)=(2.9 eV, 6.0 eV), the guest dye 15 (i.e., the blue fluorescent material of CFLA-NPh2) has the ($E_{LUMO}$, $E_{HOMO}$)=(2.49 eV, 5.33 eV).

Continuously referring to FIG. 9, which illustrate the diagram of Table 2, wherein Table 2 records the corresponding PE, CE and EQE of the OLED 1 with different guest dye 15 (i.e., the blue fluorescent material).

Figure 10:
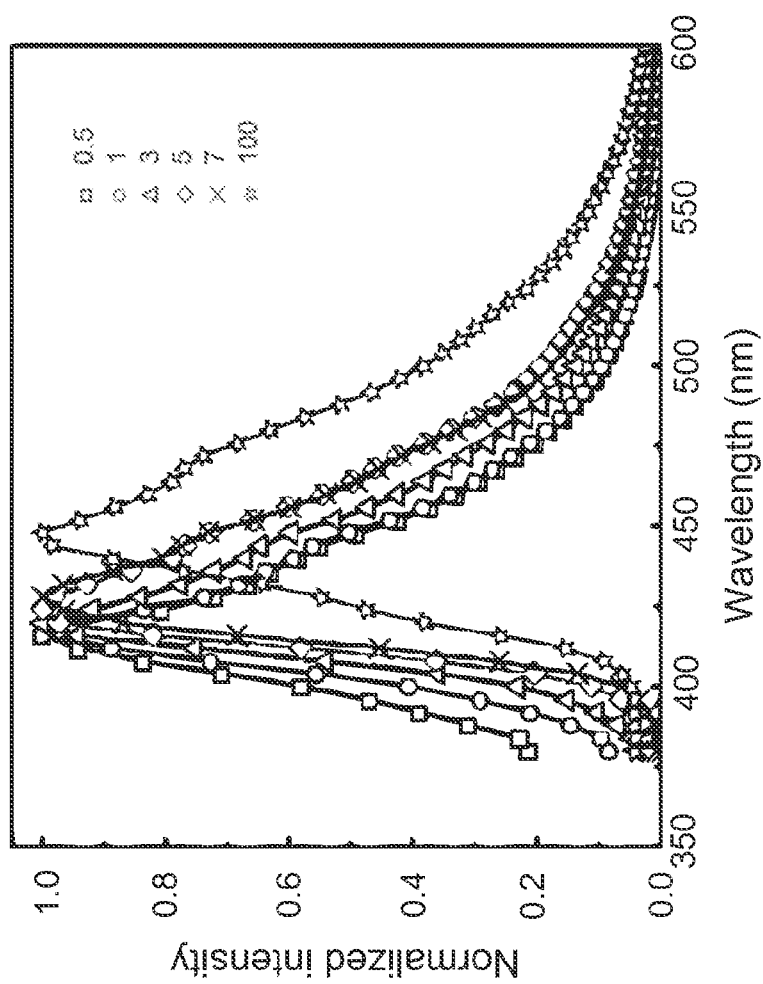
Figure 11:
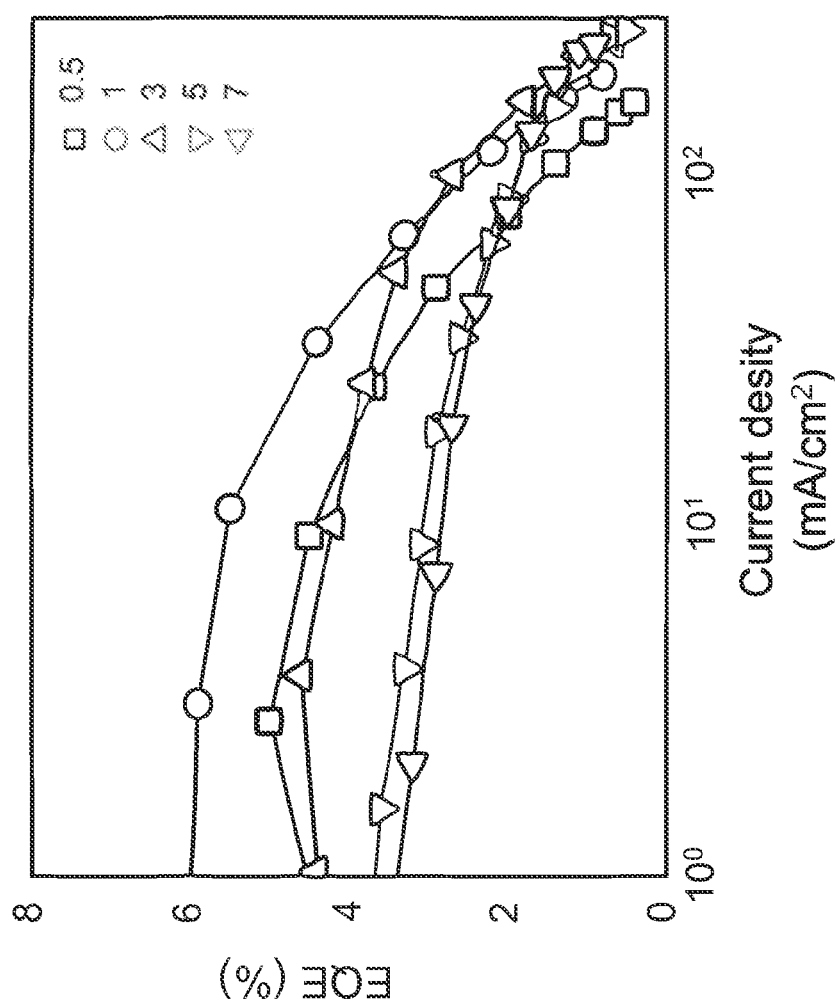

From Table 2, it can easily find that the OLED 1 using C3FLA-2 as the guest dye 15 is able to perform high PE, CE and EQE, and emit a deep blue light with CIE coordinates of (0.156, 0.055). Moreover, as light spectra graph shown by FIG. 10, the peak value of the light wavelength of the OLED 1 is more and more high with the increase of the C3FLA-2's doping concentration (increased from 1 wt % to 100 wt %). Furthermore, according to the data plot of EQE versus current density shown by FIG. 11, it can also find the OLED 1 performs less and less EQE value when the C3FLA-2's doping concentration is increased from 1 wt % to 7 wt %. Therefore, based on experiment results of table 2, FIG. 10 and FIG. 11, the optimal doping concentration of C3FLA-2 is determined to 1 wt %.

Figure 12:
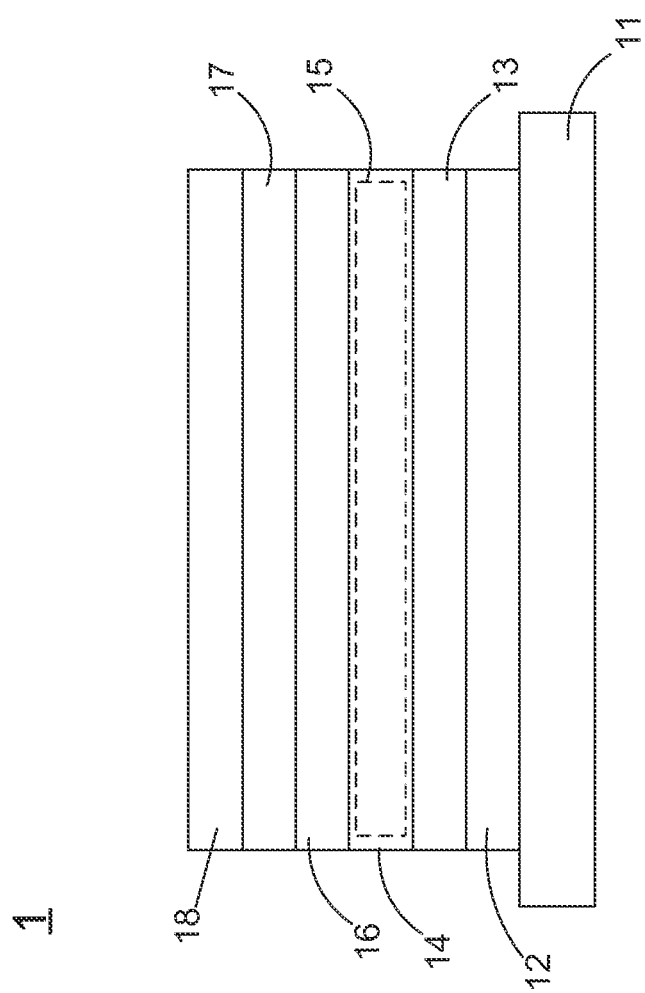
Figure 13:
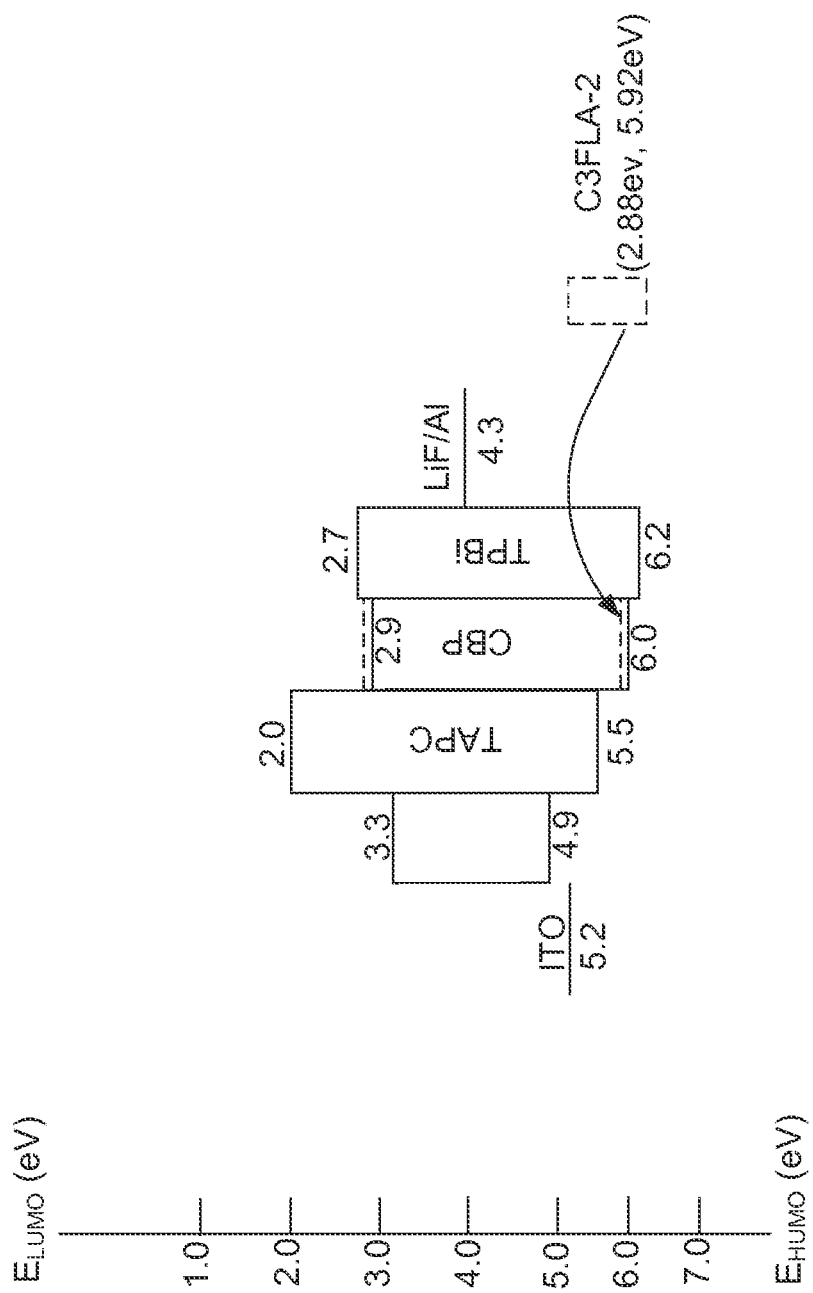

To further study the OLED 1 using the novel light-emitting material as guest dye 15, a hole transport layer is added into the OLED 1 structure shown in FIG. 5, and then a second structure for the OLED 1 is shown by FIG. 12. Moreover, FIG. 13 shows corresponding energy band diagram of the OLED 1 shown in FIG. 12. As shown in FIG. 12 and FIG. 13, the second structure of the OLED 1 consists of: an anode 11, a hole injection layer 12, a hole transport layer 13, a host light-emitting layer 14, a guest dye 15, an electron transport layer 16, an electron injection layer 17, and a cathode 18.

In the aforesaid OLED 1, indium tin oxide (ITO) substrate, lithium fluorine (LiF), and aluminum (Al) are respectively used as the anode 11, the electron injection layer 17 and the cathode 18. In addition, the hole injection layer 12 and the hole transport layer 13 are respectively made of poly(3,4-ethylenedioxythiophene) (PEDOT) and 1,1-bis{4-[di(p-tolyl)amino]-phenyl}cyclohexane (TAPC), and the electron transport layer 16 is formed by using 1,3,5-tris(N-phenylbenzimidazol-2-yl)benzene (TPBi) as the manufacturing material. Moreover, 4,4'-Bis(9H-carbazol-9-yl)biphenyl (CBP) and C3FLA-2 are as the host light-emitting layer 14 and the guest dye 15 of the OLED 1. Herein, it needs to further explain that, the TAPC is not only used as the hole transport layer 13 but also an electron confining layer (ECL).

Figure 14:
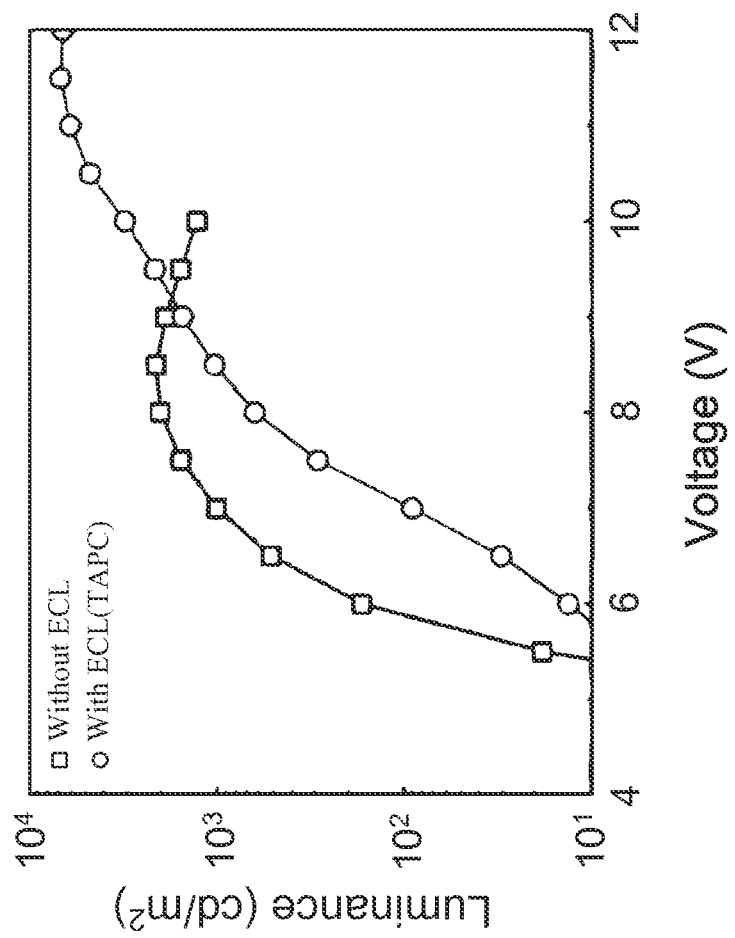
Figure 15:
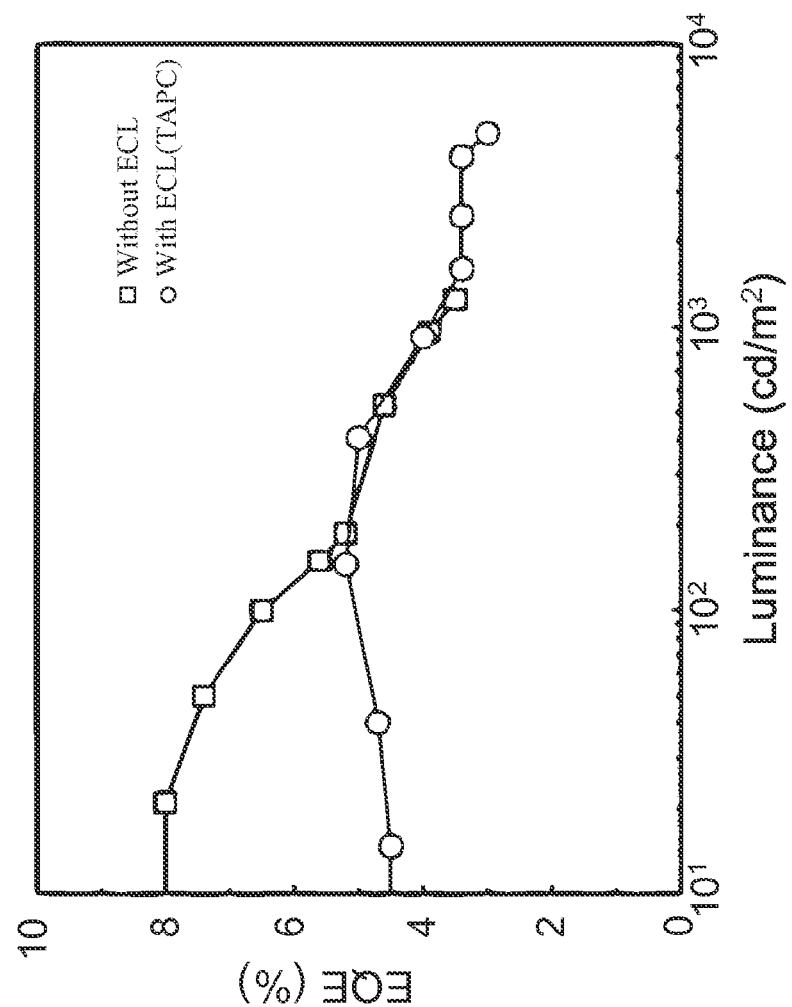

Please refer to the data plot of luminance versus voltage shown by FIG. 14 and the data plot of EQE versus current density shown by FIG. 15. From FIG. 14, it can find that the luminance of the blue light emitted by the OLED 1 with ECL is higher than the luminance of the blue light emitted by the OLED 1 without ECL. Moreover, from FIG. 15, it can also find that the EQE of the OLED 1 with ECL is almost equal to the EQE of the OLED 1 without ECL when the current density is greater than 1000 mA/cm$^2$.

Continuously referring to FIG. 16, which illustrates the diagram of Table 3, wherein Table 3 records the corresponding PE, CE and EQE of the OLED 1 with/without ECL.

From Table 3, it can easily find that the CIE coordinates of the OLED 1 with ECL is almost the same to the CIE coordinates of the OLED 1 without ECL under 1 wt % of C3FLA-2 (i.e., the blue fluorescent material) doping concentration. Therefore, based on the experiment results of Table 3, FIG. 14 and FIG. 15, it can clearly know that the OLED 1 using the novel light-emitting material proposed by the present invention as the guest dye 15 can indeed emit a high-luminance deep blue light, no matter the OLED 1 including ECL or not.

Therefore, through above descriptions, the novel light-emitting material proposed by the present invention has been introduced completely and clearly; in summary, the present invention includes the advantages of:
(1) The novel light-emitting material is a blue fluorescent material including a high quantum yield of ~86%, which can be doped into a host light-emitting layer of an organic light emitting diode (OLED) for being a guest light-emitting material, so as to increase the external quantum efficiency, the power efficiency and the current efficiency of the OLED. Most importantly, a variety of experiment results have proved that the OLED having the novel light-emitting material can emit a deep blue light with CIE coordinates of (0.156, 0.055).
(2) Moreover, the experiment results also proved that the novel light-emitting material can be applied in fabricating OLED through dry process and/or wet process; so that, the novel light-emitting material is helpful to the low-cost mass production of OLEDs.

The above description is made on embodiments of the present invention. However, the embodiments are not intended to limit scope of the present invention, and all equivalent implementations or alterations within the spirit of the present invention still fall within the scope of the present invention.

What is claimed is:

1. A novel light-emitting material, being a blue fluorescent material, wherein the chemical structure of the blue fluorescent material is represented by following chemical formula 5, chemical formula 6, or chemical formula 7:

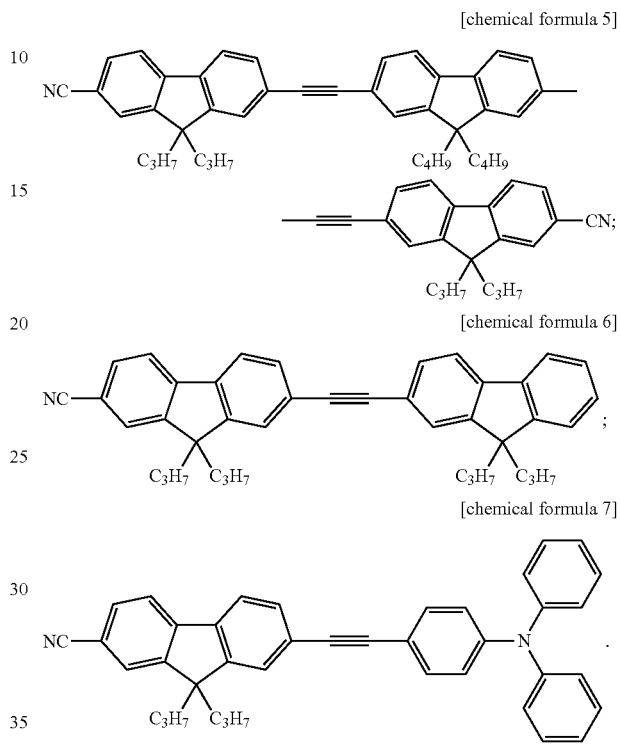

2. The novel light-emitting material of claim 1, wherein the chemical structures of the blue fluorescent material represented by the chemical formula 5, the chemical formula 6 the chemical formula 7 have a high occupied molecular orbital energy level ($E_{HOMO}$) ranged from 5.3 eV to 5.95 eV and a lowest unoccupied molecular orbital energy level ($E_{LUMO}$) ranged from 2.45 eV to 2.9 eV.

* * * * *